(12) United States Patent
Tegg et al.

(10) Patent No.: US 8,353,894 B2
(45) Date of Patent: Jan. 15, 2013

(54) CATHETER PLATFORM AND METHOD OF MANUFACTURE

(75) Inventors: Troy T. Tegg, Elk River, MN (US);
Allan M. Fuentes, Mound, MN (US);
Richard E. Stehr, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1101 days.

(21) Appl. No.: 11/618,516

(22) Filed: Dec. 29, 2006

(65) Prior Publication Data

US 2008/0161761 A1 Jul. 3, 2008

(51) Int. Cl.
*A61M 25/00* (2006.01)
*A61M 31/00* (2006.01)
(52) U.S. Cl. .................... 604/528; 604/95.04
(58) Field of Classification Search .............. 604/528, 604/533–535, 95.01–95.05; 600/146
See application file for complete search history.

(56) References Cited

U.S. PATENT DOCUMENTS

| | | | | |
|---|---|---|---|---|
| 3,470,876 A | * | 10/1969 | Barchilon | 604/95.04 |
| 3,924,632 A | * | 12/1975 | Cook | 604/527 |
| 3,983,864 A | * | 10/1976 | Sielaff et al. | 600/364 |
| 4,709,698 A | * | 12/1987 | Johnston et al. | 606/41 |
| 5,720,301 A | * | 2/1998 | van't Hooft | 600/585 |
| 6,923,788 B2 | * | 8/2005 | Kantor | 604/103.04 |
| 2004/0097965 A1 | * | 5/2004 | Gardeski et al. | 606/129 |
| 2005/0060885 A1 | | 3/2005 | Johnson et al. | |
| 2005/0065508 A1 | * | 3/2005 | Johnson et al. | 606/41 |
| 2005/0124918 A1 | * | 6/2005 | Griffin et al. | 600/585 |

* cited by examiner

*Primary Examiner* — Nicholas Lucchesi
*Assistant Examiner* — Jenna Zhang
(74) *Attorney, Agent, or Firm* — Marsh Fischmann & Breyfogle LLP (57) ABSTRACT

A catheter shaft design facilitates allows for simultaneous stringing of wires and maintains a desired spacing and separation of the wires. In one implementation, a catheter shaft (504) and a core structure (500) are formed in separate manufacturing sequences. The core structure (500) includes a number of receptacles (506) formed in an external surface thereof and may further include a central lumen (508). Wires (501*a,b*, and 502*a,b*) are placed into the receptacles (506) and the core structure (500) with wires (501*a,b* and 502*a,b*) are inserted into the lumen of the catheter shaft (504). The wires (501*a,b*, and 502*a,b*,) can then be connected to electrodes or attached to a catheter tip so as to permit steering of the tip. The design can serve as a platform for various types of catheter.

12 Claims, 12 Drawing Sheets

CATHETER PLATFORM AND METHOD OF MANUFACTURE

BACKGROUND OF THE INVENTION a. Field of the Invention

The present invention relates to catheters and, in particular, to a catheter shaft that facilitates stringing of wires as well as establishing and maintaining proper positioning of wires in a catheter shaft. The invention also provides improved catheter construction techniques.

b. Background Art

Catheters are typically threaded through a blood vessel of a patient to reach a desired site for a medical procedure. For example, in the diagnosis and treatment of atrial fibrillation, a catheter may be routed through a vessel from a patient's leg or neck to access chambers of a patient's heart. Electrodes at the distal end of the catheter can then be used for a variety of purposes including electrical mapping and ablation. The catheter therefore may include one or more internal lumens to accommodate wires (e.g., electrode wires, pull wires for steering or other structures extending through the catheter shaft), as well as to permit irrigation as may be useful for certain procedures.

More specifically, an electrode catheter typically includes a handle set at a proximate end of the catheter, one or more electrodes associated with an electrode tip at the distal end of the catheter and a shaft extending therebetween. The physician uses the hand set to manipulate the catheter and position electrodes at the desired location for the medical procedure. The shaft extends from the handle set to the electrode tip through the patient's blood vessel.

The shaft is typically constructed by extruding layers of polymer onto a core rod. A metal braid may be embedded in the polymer for improved incompressibility. The core is then removed to provide a central lumen. Various wires, for example, electrode and/or pull wires are then threaded through the central lumen. Generally, each wire is threaded through the central lumen and positioned as desired within the lumen. In the latter regard, a specific relative positioning of the pull wires (e.g., diametrically opposed) may be desired for optimal performance. In addition, it may be desired to spatially separate the wires, for example, to reduce the risk of short circuits. Additional liners, cords or other structures (e.g., to define a lumen for irrigation fluids) may be inserted into the central lumen of the catheter shaft, and reflowing of the inner liner of the cathede shaft may be necessary to ensure proper adhesion. It will be appreciated that this processing is complicated and labor intensive. Moreover, there are numerous opportunities for error, which could affect catheter performance.

In addition, the catheter shaft is designed with a number of objectives in mind. First, the shaft is generally dimensioned with an outside diameter that allows the catheter to be threaded through the vessels necessary to perform the desired medical procedures. It is also desired to provide an inside diameter sufficient to accommodate electrode wiring, steering wiring and/or irrigation fluid channels, depending on the intended use of the catheter. Therefore, a limited radial thickness of the catheter shaft is desirable.

At the same time, the shaft should provide certain mechanical properties for optimal functioning. In particular, the shaft should resist compression during use and transmit torque. With regard to resisting compression, it is important for the physician to be able to advance the catheter through the vessel, sometimes against significant frictional resistance, without undue axial compression or snaking of the catheter shaft. Such compression can complicate positioning of the distal end of the catheter at the desired location for a medical procedure. In addition, skilled physicians often rely, to some extent, on tactile feedback to attain and verify proper positioning of the catheter, and such feedback can be impaired by excessive compressibility.

The shaft should also be capable of reliably transmitting torque. In this regard, a physician normally navigates the distal end of the catheter to a desired location in part by turning a handle set at the proximal end of the catheter. Again, substantial frictional forces sometimes resist transmission of torque across the length of the catheter. In some cases, these forces can cause the shaft to twist about a longitudinal axis of the shaft, storing energy in the process in spring-like fashion. If this energy is released suddenly, the distal end of the catheter, which may be bent by a steering mechanism, can be propelled with significant force against unintended tissue. This can have dire consequences in the context of intracardiac procedures.

In order to provide the desired mechanical properties within the noted dimensional constraints, some catheters incorporate a dual braided shaft design involving an inner braided wire and an outer braided wire. Each of braided wires is typically embedded, to some extent, in a polymer so that the braided wire and polymer function as a system to impart desired mechanical properties. More specifically, the inner braided wire system is typically the primary source of compression resistance. The outer braided wire system, having a larger moment arm relative to the longitudinal axis of the shaft, is typically the principal source of torque transmission. Each of the inner and outer braided wire systems may be designed to satisfy its primary function in this regard.

The dual braided shaft is generally formed by extruding a polymer liner onto a rod. The outer braid is then formed on the polymer liner, and an outer polymer jacket is then extruded onto the outer braid. Thereafter, the rod is removed to leave a hollow interior. A coil is then inserted into the hollow interior to form the inner braid, and the polymer liner is reflowed along the length of the shaft to integrate, to some extent, the inner braid into the catheter shaft structure. The various wires and an irrigation tube may then be threaded through the central lumen of the shaft.

BRIEF SUMMARY OF THE INVENTION

The present invention relates to a catheter shaft design, and related construction processes, that facilitate stringing and proper positioning of one or more wires in the catheter shaft. The invention simplifies catheter construction, improves wire placement and separation, and reduces the likelihood of construction defects or catheter malfunctions. Moreover, the invention provides a single design platform for substantially any type of catheter including fixed curve, steerable, bi-directional, diagnostic, ablation (irrigated or non-irrigated) and luminal designs. The invention also provides great design flexibility to provide a catheter shaft with desired incompressibility, torsional rigidity and flexibility for a variety of catheter applications.

In accordance with one aspect of the present invention, a catheter apparatus includes structure for securing at least one wire, e.g., an electrical or steering wire. The apparatus includes a catheter shaft having a lumen extending therethrough and a core structure, disposed with the lumen of the catheter shaft, for securing at least one wire in a substantially fixed position in relation to the catheter shaft. The core structure may extend axially through a portion of or through substantially the entirety of the catheter shaft. In addition for at least an axial section of the core structure, the core structure may include outside surface portions for maintaining the core structure in a fixed spatial relationship with respect to the catheter shaft. For example, those outside surface portions may butt against inside surface portions of the catheter shaft or may adhere (e.g., due to polymer reflowing) to the inside surface portion of the catheter shaft, at least at portions of the interface therebetween.

In one embodiment, the core structure is formed from extruded polymer and the wire is captured between the core structure and the catheter shaft. A receptacle, such as a longitudinal channel formed on the exterior of the core structure, may be provided to accommodate the wire. Such a receptacle can also be used to establish and maintain the proper wire positioning and protects against undesired contact of the wire with other elements that could result in interference or short circuits. Multiple receptacles may be provided to accommodate multiple wires. In addition, the core structure provides a further element that may be used, together with elements of the catheter shafts, to impart desired mechanical properties to the overall catheter, e.g., desired incompressibility, torsional rigidity and/or flexibility. For example, the material properties (e.g., polymer durometer) and dimensions (shape, thickness, etc.) of the core structure may be varied in this regard.

In accordance with another aspect of the present invention an apparatus is provided for maintaining a desired positioning and separation between multiple wires. The apparatus includes an elongate body dimensioned to be received within a lumen of a catheter shaft and receptacle structure associated with the elongate body, defining first and second receptacles for receiving first and second wires. The receptacles are adapted to maintain the first and second wires in a substantially fixed, spaced relationship with respect to one another.

For example, the first and second wires may be pull wires and the receptacles may maintain the pull wires in a diametrically opposed relationship. As a further example, the wires may be electrode wires and the receptacles may maintain the wires in a spaced relationship. Additionally or alternatively, the receptacles may maintain a pull wire and an electrode wire in a spaced relationship, for example, to reduce the likelihood of short circuits. In one embodiment, the apparatus comprises a generally cylindrical structure, formed from extruded polymer material, with a number of parallel channels (e.g., four) in its external surface. The channels may be substantially evenly spaced about the periphery of cylindrical structure. In addition, a central lumen may be used for accommodating irrigation fluid pathways or other structures.

In accordance with a still further aspect of the present invention, a method is provided for use constructing a catheter with multiple wires. The method involves providing a catheter shaft having a lumen extending therethrough and simultaneously stringing first and second wires through the lumen of the catheter shaft while maintaining a defined relative spatial relationship between the first and second wires. In this manner, construction of the catheter is expedited and manufacturing defects are potentially reduced.

Such simultaneous stringing of the wires may be accomplished in various ways. For example, the wires may be held in a fixed position while the catheter shaft is passed, in a spatially controlled fashion (e.g., by machinery) over the wires. Alternatively, the wires may be held taught as they are drawn through the shaft lumen in spatially controlled fashion. As a further alternative, an insertion tool may be utilized to hold the wires as they are manually or automatically inserted in the shaft lumen.

In accordance with a further aspect of the present invention, an elongate core structure is used to insert a wire through a catheter shaft lumen. An associated construction process involves providing a catheter shaft having a lumen, securing a wire to the elongate structure and inserting the elongate structure, with the secured wire, into the catheter shaft lumen. For example, the wire may be secured to the elongate structure by placing the wire into a channel of the elongate structure that is dimensioned to receive the wire. The wire may be adhered in the channel, held tightly in the channel or may be loosely placed within the channel.

The elongate core structure may include multiple receptacles for holding multiple wires. In one implementation, the wires are held in receptacles of an elongate structure as the structure is manually or automatically inserted through the lumen of the catheter shaft. In this regard, the position of the wires in relation to the catheter shaft may be constrained due to a close fit between the elongate structure and the catheter shaft. This enables multiple wires to be simultaneously threaded while maintaining a defined spatial relationship between the wires.

According to yet another aspect of the invention, a method for constructing a catheter with multiple wires is provided. The method involves: providing a core structure defining first and second receptacles for maintaining wires in a fixed spaced relationship with respect to one another; providing first and second wires in the respective first and second receptacles; and providing a shaft structure radially outside of the core structure and the first and second wires. Those steps may be performed in various sequences. For example, wires may be inserted into the core structure receptacles, and then the core structure may be inserted into the lumen of the shaft structure as described above. Alternatively, the core structure and shaft structure may be formed in a single, sequential construction process. In such a case, the wires may be assembled as part of the single construction sequence (e.g., between formation of the core structure and assembly of the shaft structure over the core structure) or may be inserted into the receptacles after the noted sequence. In any event, the receptacles serve to position the wires and isolate the wires from one another. The core structure preferably includes a lumen that may be used for irrigation and other purposes.

The foregoing and other aspects, features, details, utilities, and advantages of the present invention will be apparent from reading the following description and claims, and from reviewing the accompanying drawings.

DETAILED DESCRIPTION OF THE INVENTION

In the following description, the invention is set forth in the context of specific implementations involving separate construction sequences for a dual braided catheter shaft and a core structure, followed by assembly of those components to realize a steerable, irrigated electrode catheter. While this is an advantageous implementation of the invention, and serves to illustrate the various aspects of the invention, it should be appreciated that the invention is not limited to this catheter application, this type of catheter shaft, this specific core structure or this construction technique. Accordingly, the description below should be understood as exemplifying the invention and not by way of limitation.

More specifically, the following discussion first includes a brief description of an exemplary catheter context. Thereafter, a dual braided catheter shaft and construction sequence are described, followed by a description of a core structure and associated construction sequence. Finally, a process for assembling the shaft, core structure and related components is described.

Figure 4:
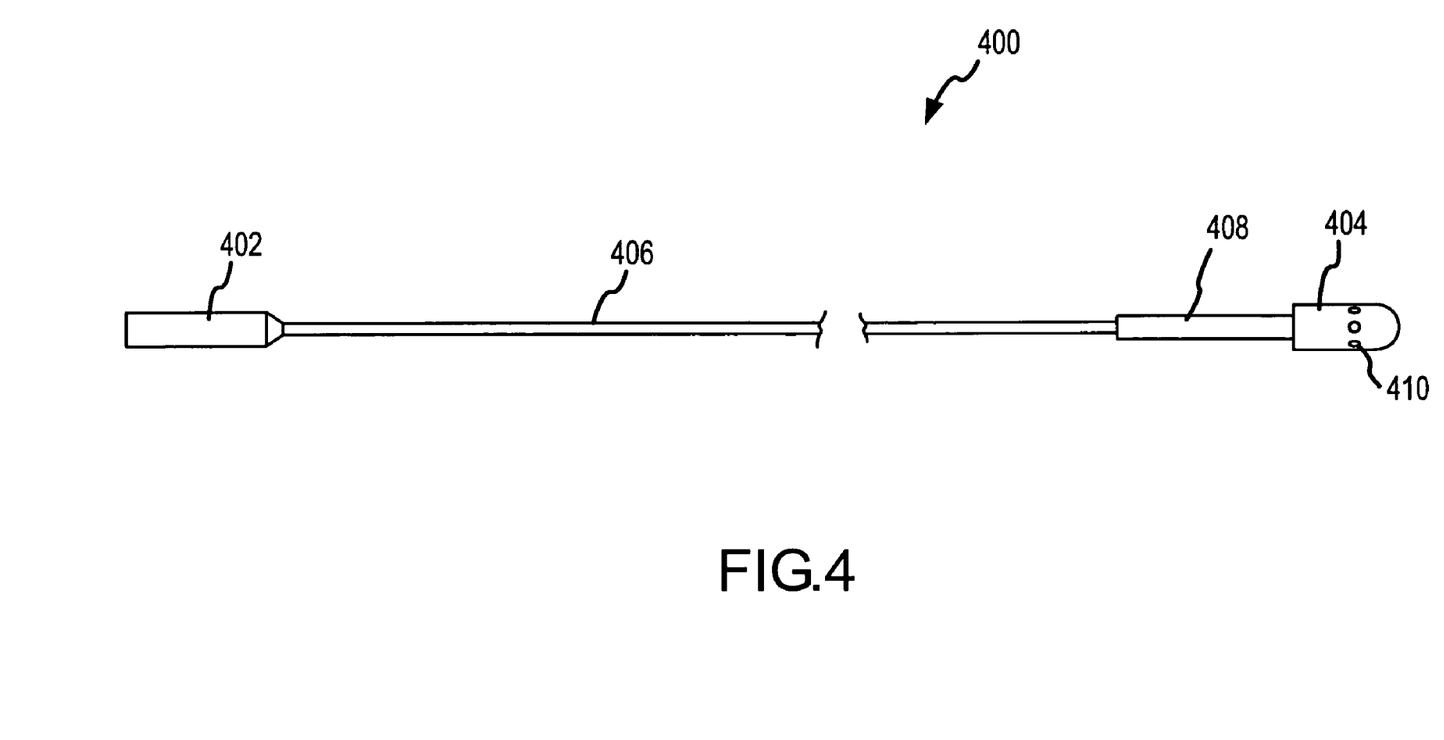
FIG. 4 shows an electrode catheter including a catheter shaft constructed in accordance with the present invention.

FIG. 4 shows an electrode catheter 400 that may employ a catheter shaft/core structure assembly 406 constructed in accordance with the present invention. Generally, the catheter 400 includes a handle set 402, an electrode tip 404, and the assembly 406 that extends between the handle set 402, at the proximal end of the catheter shaft 406, and the electrode tip 404 at the distal end of the assembly 406. The illustrated electrode tip includes irrigation orifices 410 for providing irrigation for certain procedures such as certain ablation procedures. A catheter jacket assembly 408 accommodates pull wire connections, electrode connections (e.g., contact brazing or welding), irrigation pathway connections, and the like. The catheter 400 may include other components that are omitted from the drawing for the sake of simplicity.

The catheter is used to position the electrode tip 404 at a desired location for a medical procedure, e.g., in the case of diagnosing or treating atrial fibrillation the catheter tip 404 may be positioned against an internal wall of the patient's heart. This location may be accessed, for example, by threading the assembly 406 through a blood vessel of the patient from a location in the patient's leg or neck. It will be appreciated that a variety of different types of electrode assemblies may be used in connection with the catheter 400 depending on the specific application involved. For example, one or more ablation and/or mapping electrodes may be disposed at the distal end of the catheter shaft 406. Accordingly, the illustration of a particular electrode tip 404 is not intended to imply any limitation in this regard.

In use, the physician manipulates the handle set 402 to advance, withdraw, rotate and otherwise position the electrode tip 404 at a desired location. It will be appreciated that significant frictional resistance may sometimes be experienced in connection with such manipulation. In addition, experienced physicians rely to some extent on tactile feedback, transmitted back from the electrode tip 404 to the handle set 402 via the assembly 406, in identifying a proper electrode position for a procedure. It is therefore desirable for the assembly 406 to be sufficiently incompressible and have sufficient torsional rigidity to allow such manipulation without substantial compression or twisting and to reliably provide the tactile feedback that is useful to physicians. Both the shaft and the core structure can be designed to cooperatively provide the desired mechanical properties. The discussion immediately below describes a suitable shaft in this regard as well as associated construction techniques. Thereafter, the core structure and its construction are discussed.

Figure 1:
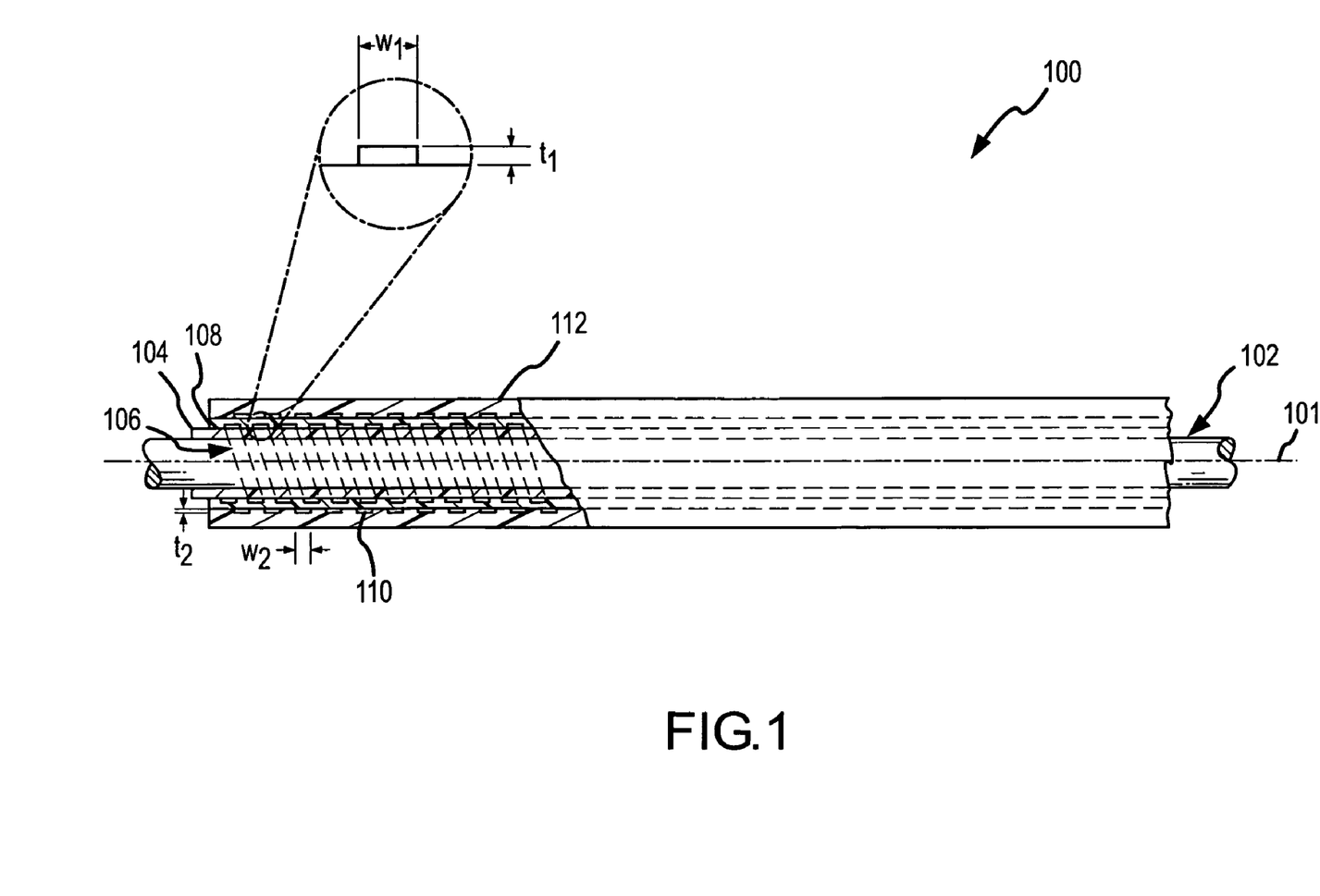
FIG. 1 is a side cross-sectional view of a dual braided catheter shaft in accordance with the present invention.

Referring to FIG. 1, a side, partially cross-sectional view of a dual braided catheter shaft 100 in accordance with the present invention is shown. FIG. 1 also shows a core rod 102 used during construction of the shaft 100. The rod 102 is removed after construction and is not a part of the shaft 100. Rather, a central lumen remains after the rod 102 is withdrawn. This lumen may be used for a variety of purposes, including wiring for electrodes, pull wires, irrigation fluid passageways and the like. It will be appreciated that multiple lumens may be provided in the area vacated by the rod 102. Alternatively, the shaft 100 may be constructed on a hollow rod that remains as part of the shaft 100. The hollow rod defines a hollow interior for passage of irrigation fluids or wires. The hollow rod may also include a number of longitudinal channels, e.g., formed on the external surface thereof, for routing of electrode wires, pull wires and the like. The various layers of the illustrated shaft 100 can then be formed on the hollow rod.

The illustrated shaft 100 is formed from a number of layers of material sequentially formed on the core rod 102. These layers include an inner jacket 104 formed on the rod 102, an inner braid 106 formed on the inner jacket 104, an intermediate jacket 108 formed over the inner braid 106, an outer braid 110 formed on the intermediate jacket 108 and an outer jacket 112 formed over the outer braid 110. These layers 104, 106, 108, 110 and 112 thus form an integral catheter shaft system with minimal, if any, air pockets between the layers.

The inner jacket 104 is formed from a melt processable polymer extruded directly onto the rod 102. For example, the inner jacket 104 may be formed from any of various polymers having a durometer selected to impart desired mechanical properties to the shaft 100, as will be described in more detail below. Suitable polymers include those well known in the art, such as polyurethanes, polyether-block amides, polyolefins, nylons, polytetrafluoroethylene, polyvinylidene fluoride and fluorinated ethylene propylene polymers, and other materials. A braiding machine can then be operated to wind a wire around the inner jacket 104 so as to form the inner braid 106. For example, the inner braid 106 may be constructed by winding a flat wire formed from any of various metals such as stainless steel.

The second jacket 108 is formed from a melt processable polymer (example set forth above) and can be extruded over the inner jacket 104 and inner braid 106. In this manner, the inner braid 106 is embedded in the intermediate jacket 108 with few or substantially no air pockets for potentially improved mechanical characteristics. The material used for the intermediate jacket 108 can be the same as or different than the inner jacket 104, and it can have the same or a different durometer.

After the intermediate jacket 108 has been formed, a braiding machine can be operated to wind a wire on the intermediate jacket 108 to form the outer braid 110. For example, a flat wire formed from metal such as stainless steel can be used in constructing the outer braid 110. The material of the wire used to form the outer braid 110 can be the same as or different than the material used to form the wire of the inner braid 106. In addition, the dimensions and winding parameters of the outer braid 110 can be the same as or different than those for the inner braid 106. Some considerations in this regard will be discussed in more detail below.

After the outer braid 110 has been applied, the outer jacket 112 is formed on the intermediate jacket 108 and outer braid 110. For example, the outer jacket 112 may be formed from a melt processable polymer (examples set forth above) and may be extruded directly onto the intermediate jacket 108 and outer braid 110. In this manner, the outer braid 110 is substantially fully embedded in the outer jacket 112 with few or substantially no air pockets therebetween for potentially enhanced mechanical properties. The outer jacket 112 may be formed from the same material as the intermediate jacket 108 and/or inner jacket 104 or different materials may be used. In addition, the outer jacket 112 may have the same or a different durometer than the intermediate jacket 108 and/or inner jacket 104.

The properties of the various layers 104, 106, 108, 110 and 112 can be selected to impart desired properties to the completed shaft 100. In this regard, it is generally desirable that the shaft 100 be substantially incompressible. In addition, it is generally desired that the shaft 100 effectively transmit torque across the length of the shaft so that a torque applied by a physician on the handle set at the proximate end of the shaft is effectively transmitted to an electrode or other tool at the distal end of the shaft. That is, the shaft should resist twisting about the longitudinal axis 101 of the shaft 100 in the event of significant frictional resistance to such torque. On the other hand, it is generally desired that the shaft 100 be sufficiently flexible to allow for threading through a blood vessel of a patient and steering of the distal end of the catheter to a desired location for a medical procedure. The mechanical properties of the shaft 100 may vary along a length of the shaft in this regard.

It will be appreciated that any and all of the layers 104, 106, 108, 110 and 112 may be involved in providing the desired properties. However, in the illustrated embodiment, the inner braid system provides the primary axial rigidity for the desired incompressibility, and the outer braid system, which has a greater moment arm in relation to the axis 101, provides the primary torsionally rigidity for transmitting torque. The inner braid system includes the inner braid 106 and the intermediate jacket 108 that is extruded onto the inner braid 106. These components cooperate to provide a desired level of axial rigidity. Thus, the axial rigidity of the inner braid system is principally determined by the durometer of the intermediate jacket material, the material and dimensions of the wire used to form the inner braid 106, and the braiding parameters including the pic rate (number of windings per inch) of the inner braid 106. With regard to the material used to form the intermediate jacket 108, the higher the durometer of this material, the greater the axial rigidity of the inner braid system, all other factors being equal. Again, it is noted that a catheter designer may balance the need for shaft flexibility with the desire for axial rigidity.

With regard to the material used to form the inner braid 106, generally, the harder the material the greater the axial rigidity. The axial rigidity can also be enhanced by increasing the width $w_1$ (the axial dimension) of the wire used to form the inner braid 106 and increasing the pic rate of the inner braid 106. However, it is desirable that the thickness $t_1$ (the radial dimension) of the wire used to form the inner braid 106 should be minimized to as to reduce the overall thickness of the shaft 100. Accordingly, using a flat wire where the width $w_1$ is greater than the thickness $t_1$ allows for obtaining the desired axial rigidity without unduly increasing the thickness of the shaft 100. In the illustrated example, the thickness $t_1$ may be between about 0.0005-0.004 inches, and the width $w_1$ may be between about 0.002-0.016 inches, depending on the particular catheter application. Additionally, as will be discussed in more detail below, the pic rate may be varied along the length of the catheter, for example, to provide greater flexibility near the distal end of the catheter and greater axial rigidity towards the proximate end of the catheter. For example, depending on the application, the pic rate of the inner braid 104 may be between about 30-60 pics per inch (PPI), and this value may vary along the length of the shaft 100.

Similarly, the mechanical properties imparted to the shaft 100 by the outer braid system are principally a function of the durometer of the outer jacket material, the dimension (e.g., $t_2$ and $w_2$) of the outer braid wire, and the braiding parameters of the outer braid including its pic rate (which may vary along the length of the shaft). Although the outer braid 110 is shown as being formed from a flat wire, a round wire or other configuration may be employed. In this regard, it is noted that a primary function of the outer wire is to impart torsional rigidity, and a greater thickness $t_2$ may be desired within the constraints of the desired overall shaft thickness. In the illustrated embodiment, the outer braid wire has a thickness $t_2$ of between about 0.001-0.004 inches, a width $t_2$ of between about 0.002-0.016 inches, and the outer braid has a pic rate of between about 30-69 PPI.

The resulting shaft 100 provides the desired incompressibility and torsional rigidity properties within a reduced thickness envelope, thereby allowing for a reduced shaft outside diameter and/or an increased shaft inside diameter. In this regard, the outside shaft diameter may be no more than about 5-7 french. The inside diameter may be at least about 3 french, and the shaft thickness (the outside diameter less the inside diameter) may be about 0.008 inches.

Figure 2A:
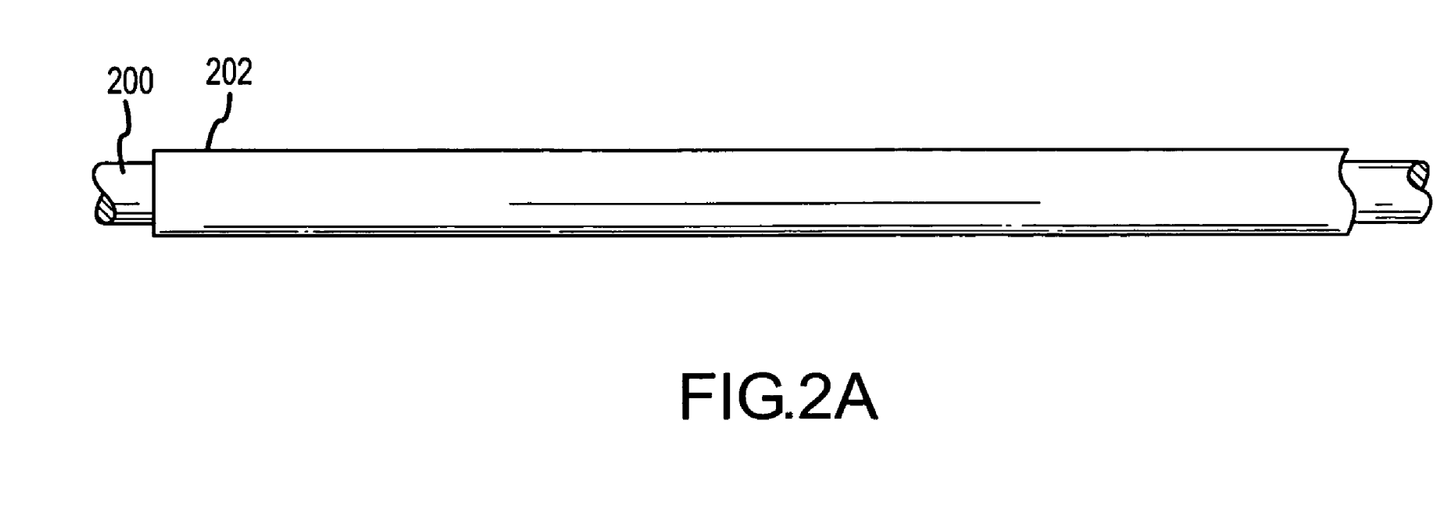
FIGS. 2A-2F illustrate a process for constructing a dual braided shaft in accordance with the present invention.
Figure 2B:
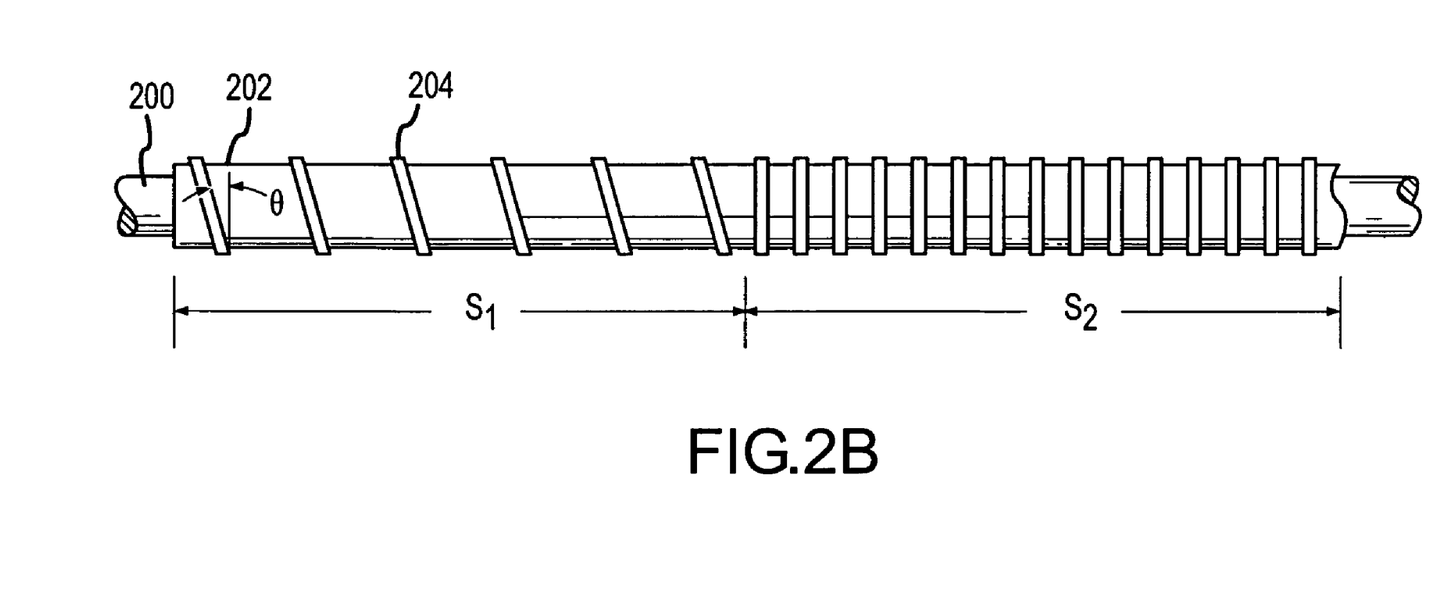

FIGS. 2A-2F graphically depict a sequence for constructing a dual braided catheter shaft 212 in accordance with the present invention. As shown in FIG. 2A, the process is initiated by extruding a melt processable polymer onto the core shaft 200 to form an inner jacket 202. Thereafter, a braiding machine is operated to braid a wire onto the inner jacket 202 to form the inner braid 204. As shown in FIG. 2B, it is possible to control the operation of the braiding machine to provide a first pic rate in a first section $s_1$ of the catheter and a second pic rate in a second section $s_2$ of the catheter. In this case, a lower pic rate is used in section $s_1$ than in section $s_2$. For example, this may be done to provide greater flexibility at a distal end of the catheter and a greater axial rigidity at a proximate end. In this regard, the greater density of wire coverage in section $s_2$ provides a higher axial rigidity whereas the lesser density of wire coverage in section $s_2$ and the greater winding angle $\theta$ provides greater flexibility in section $s_1$.

Figure 2C:
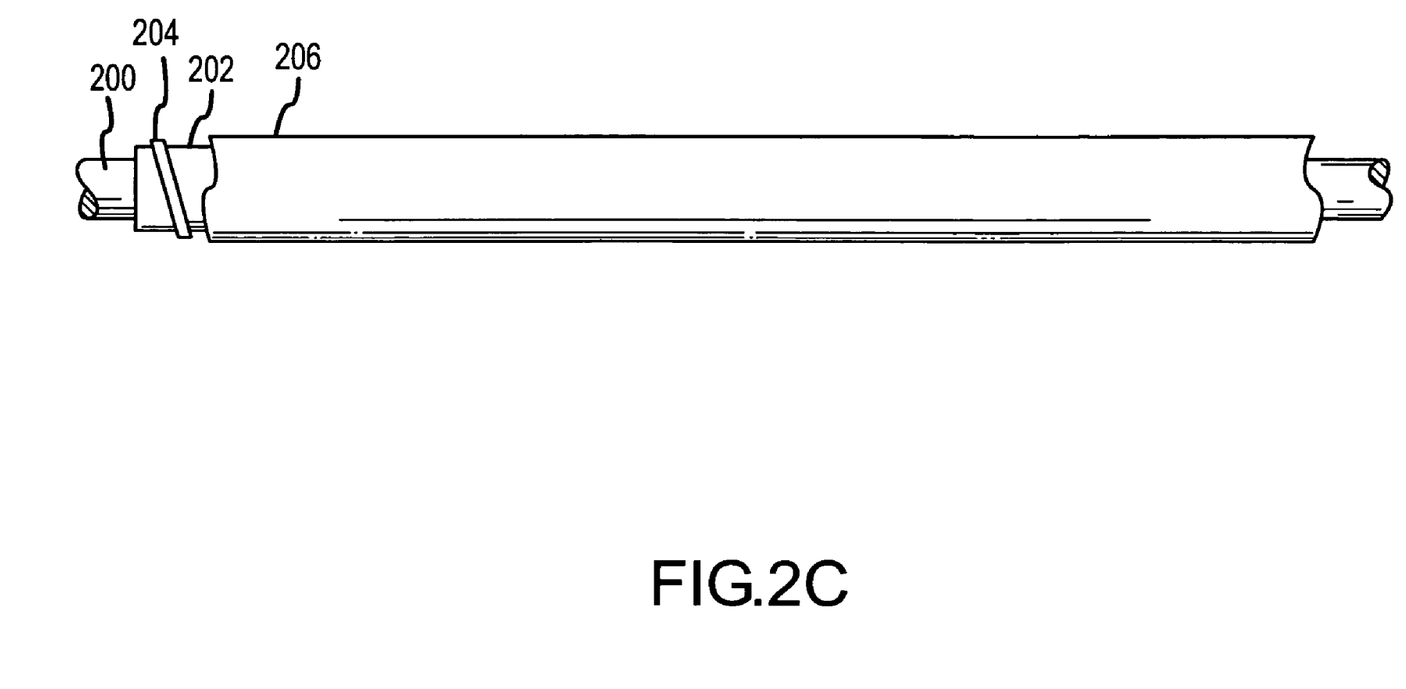
Figure 2D:
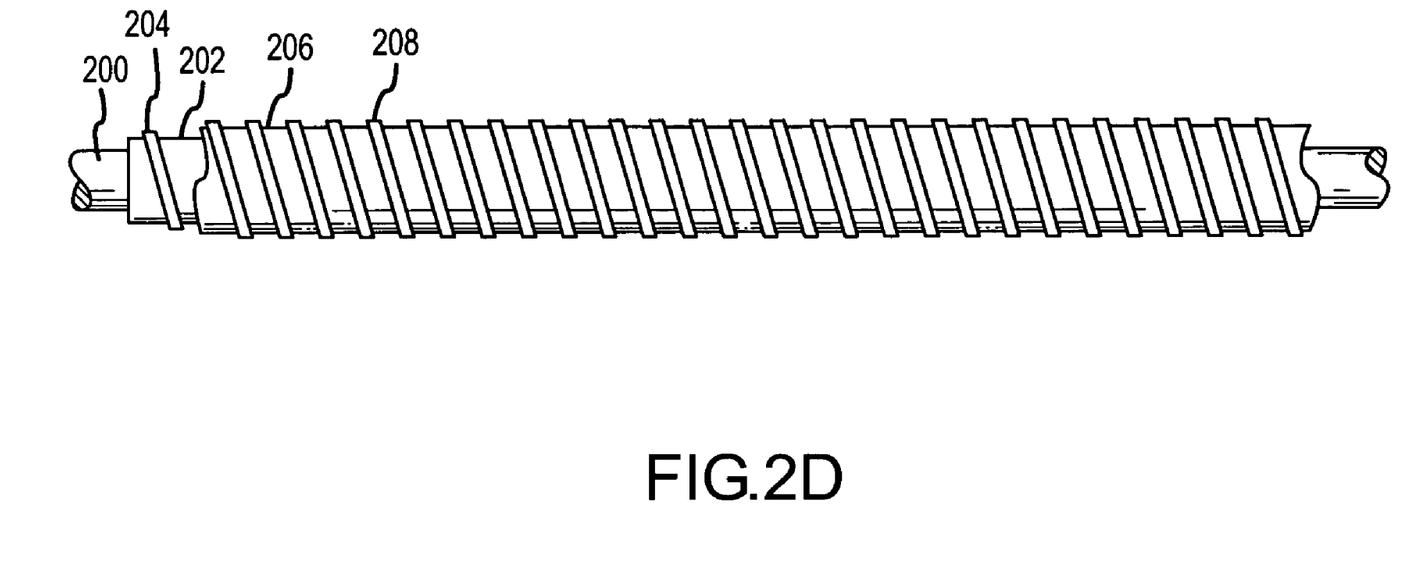

After the inner braid 204 has been formed, the intermediate jacket 206 is extruded onto the inner braid 204 and the inner jacket 202, as shown in FIG. 2C. A braiding machine can then be operated to wind a wire on the intermediate jacket 206 to form the outer braid 208, as shown in FIG. 2D. Although not shown, it will be appreciated that the pic rate of the outer braid 208 can also be varied along the length of the catheter to balance the desire for torsional rigidity with desire for flexibility. In addition, although the inner and outer braids 204 and 208 are shown as being wound in the same rotational sense in FIG. 2D, the braids 204 and 208 may be wound in opposite rotational senses, for example, to provide desired mechanical properties to the shaft 212.

Figure 2E:
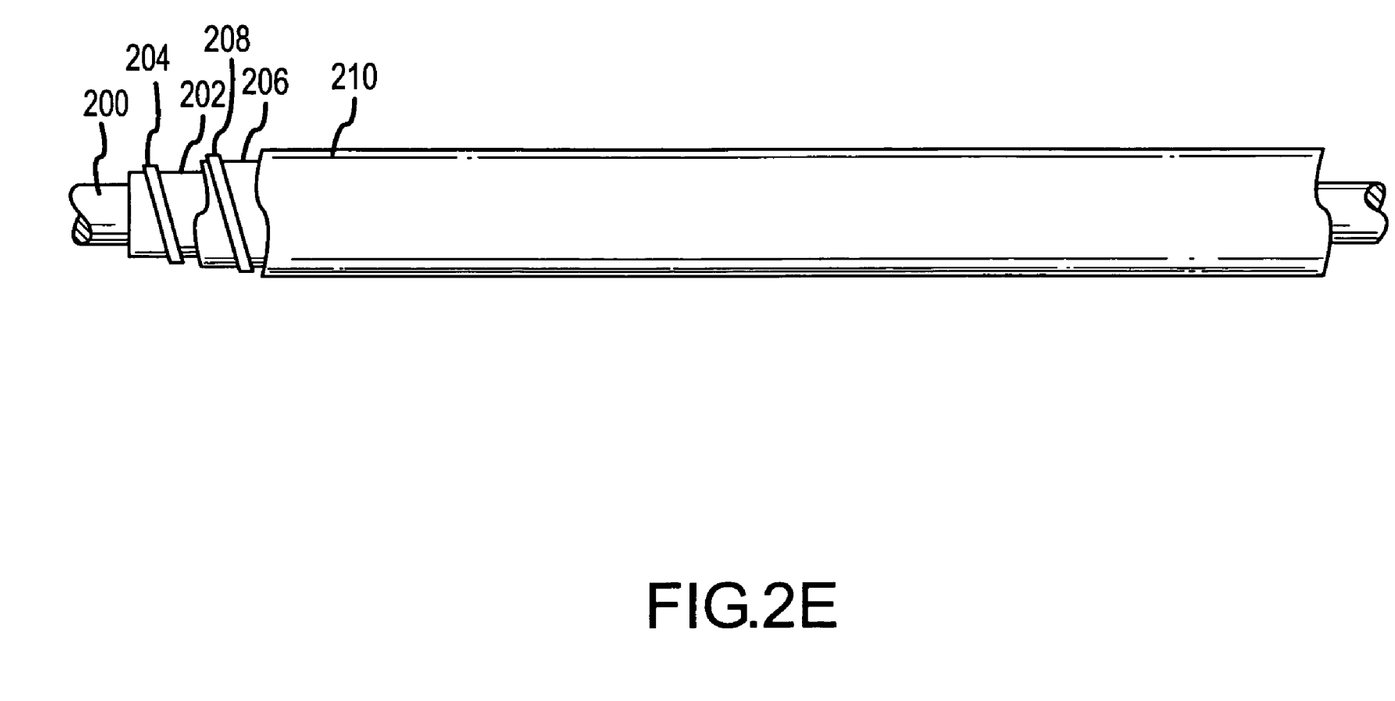
Figure 2F:
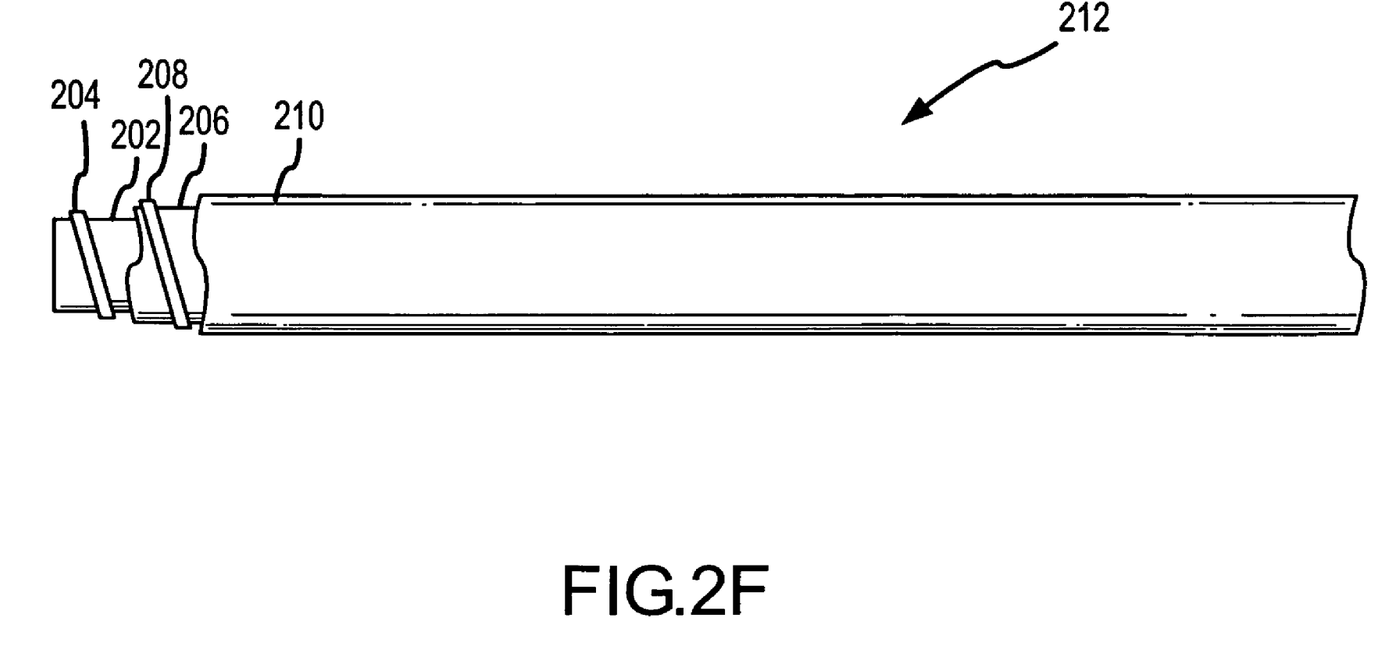

After the outer braid 208 has been formed, an outer jacket 210 is formed over the outer braid 208 and intermediate jacket 206 by extruding melt processable polymer material thereon, as shown in FIG. 2E. Finally, the core rod 200 is extracted from the assembly to form the catheter shaft 212, as shown in FIG. 2F.

Figure 3:
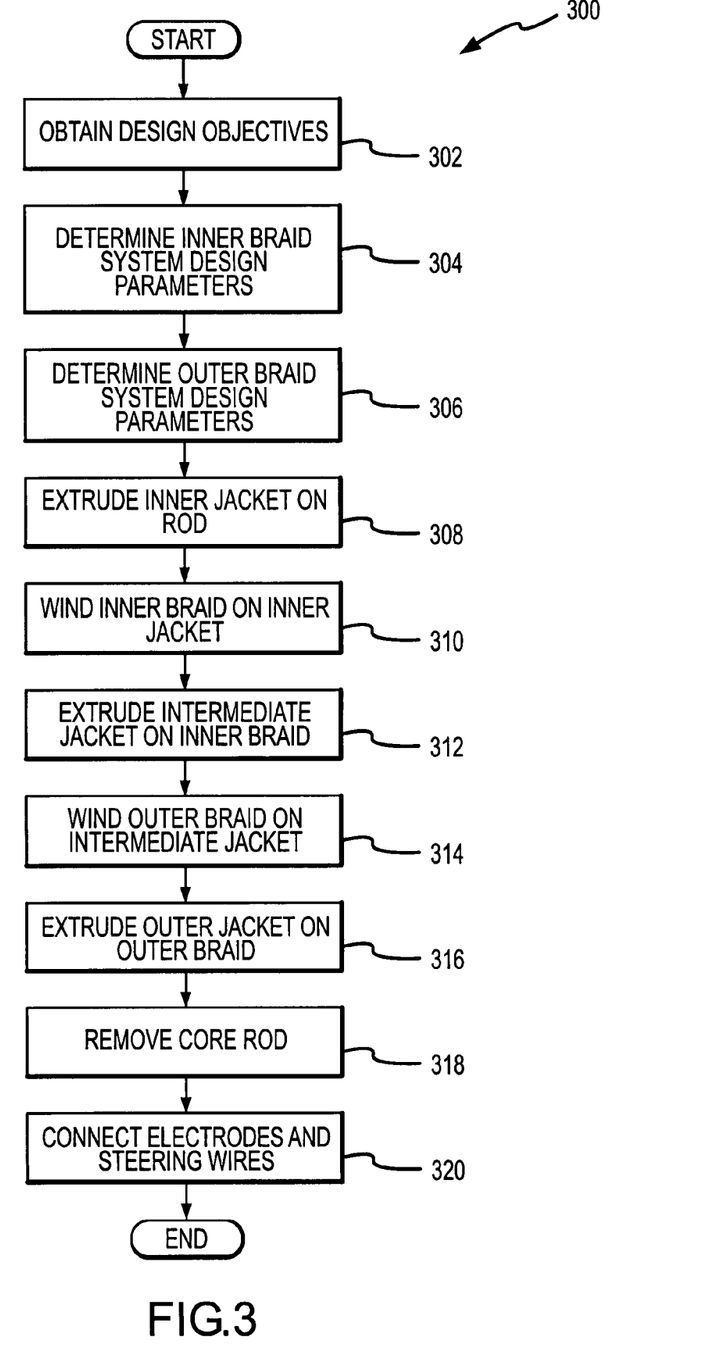
FIG. 3 is a flowchart illustrating a process for constructing a dual braided shaft in accordance with the present invention.

The overall process for designing and constructing a catheter shaft can be summarized by reference to the flowchart of FIG. 3. The illustrative process 300 is initiated by obtaining (302) design objectives for the catheter shaft. In this regard, different shaft platforms may be used for different catheter applications such as fixed curve catheters, steerable catheters, bi-directional catheters and the like. For example, the particular catheter application may dictate the need for greater flexibility or greater torsional rigidity, or may dictate a particular need for axial rigidity. In addition, the catheter application may dictate a particular limit on the outside diameter of the catheter or require an inside diameter sufficient for electrode wiring, pull wires and irrigation fluid channels. All of these objectives may be considered in relation to the design of the catheter shaft.

The designer can then determine (304) the inner braid system design parameters and determine (306) the outer braid system parameters. As noted above, the inner braid system may be used primarily to address considerations related to axial rigidity. In this regard, the durometer of the intermediate jacket material, the material used for the inner braid wire, the dimensions of the inner braid wire and the braiding parameters for the inner braid may be selected in relation to the desire for axial rigidity, on the one hand, versus catheter flexibility on the other. As illustrated above, these characteristics may vary along the length of the catheter. While it is theoretically possible to change the durometer of the intermediate jacket material along the length of catheter, as a practical matter, existing extrusion processes generally do not provide sufficient accuracy in this regard. Accordingly, in accordance with the present invention, the pic rate of the inner braid can be controlled to allow for variation of mechanical properties along the catheter shaft in a continuous flow process. This greatly increases production rates in relation to certain existing processes for varying mechanical properties by combining shaft segments in a piecewise fashion. In this regard, it is anticipated that production rates on the order of 30 feet per minute may be achieved in accordance with the present invention versus existing production rates on the order of inches per minute using existing processes.

Similarly, the outer braid system design parameters can be determined (306) in relation to the durometer of the outer jacket, the material used for the wire of the outer braid, the dimensions of the wire for the outer braid and the braiding parameters used in braiding the outer braid. These parameters may be selected to balance the desire for torsional rigidity with the desire for shaft flexibility.

After the design parameters have been determined, construction of the shaft begins by extruding (308) the inner jacket on the core rod. A braiding machine is then operating to wind or cross-braid (310) the inner braid on the inner jacket. The intermediate jacket is then formed by extruding (312) material on the inner braid an inner jacket. A braiding machine can then be again operated to wind or cross-braid (314) the outer braid on the intermediate jacket. Finally, the outer jacket is extruded (316) on the outer braid and intermediate jacket, and the core rod is removed (318) to form the catheter shaft.

Electrodes and pull wires can then be connected (320) to form the finished catheter product. The nature of these connections and additional processes will depend on the particular catheter application. For example, pull wires may be threaded through the central lumen of the catheter shaft in the case of a steerable catheter application. In addition, wiring for a single electrode or multiple electrodes may be threaded through the central lumen, depending on the application. Additional processes may be performed to define a passageway for irrigation fluid to support irrigated medical procedures. Additional reflowing steps may be required to adhere the distal catheter tip to the distal end of the catheter shaft after the electrode connections have been formed. It will be appreciated that a number of other conventional finishing processes may be implemented in this regard. The discussion below describes a core structure that greatly simplifies such processing and results in a product with improved reliability.

The discussion above set forth an exemplary catheter shaft and sequence for its construction. It will be appreciated that other catheter shaft structures may be utilized in accordance with the present invention. In any event, once a catheter shaft with a lumen extending therethrough has been formed, a core structure with wires may be inserted through the catheter shaft lumen.

Figure 5:
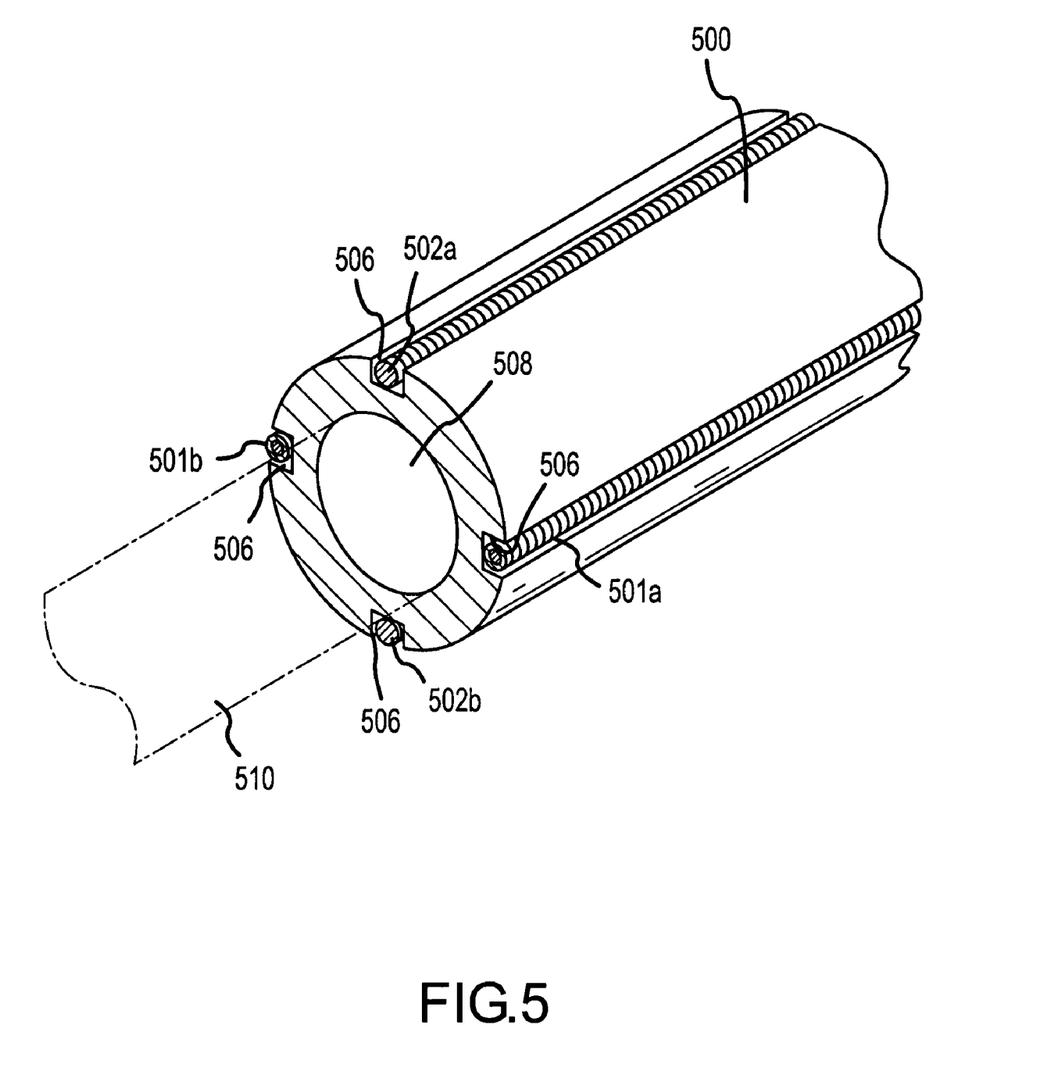
FIG. 5 is a perspective view showing a core structure in accordance with the present invention.
Figure 6:
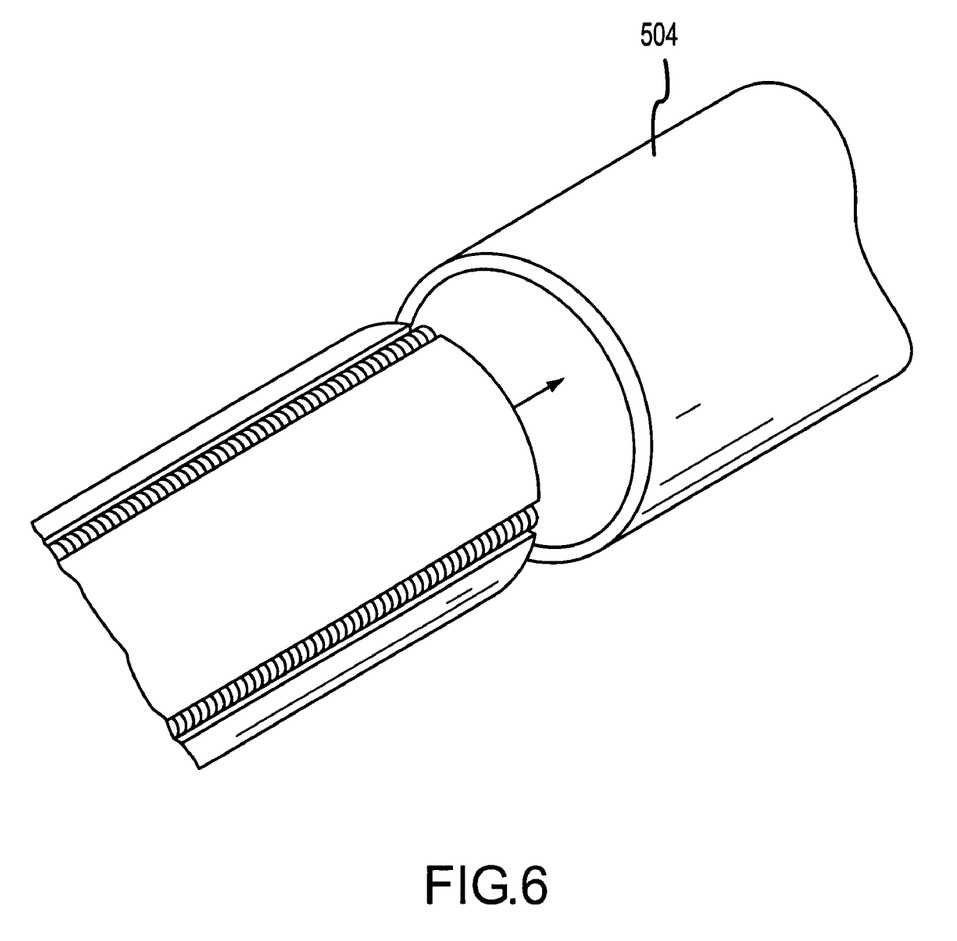
FIG. 6 is a perspective view of the core structure of FIG. 5 being inserted into a catheter shaft.

FIGS. 5 and 6 illustrate such a core structure and assembly process. Referring first of FIG. 5, a perspective view of a core structure 500 is shown. The core structure 500 is used to insert wire assemblies 501a,b and 502a,b into the catheter shaft 504 (FIG. 6) and to maintain a desired spatial relationship between the wire assemblies 501a,b and 502a,b. It will be appreciated that any suitable structure may be used in this regard. The illustrated core structure 500 is a unitary structure formed from a polymer material, such as the polymer materials discussed above in connection with the catheter shaft description. In the case of the core structure 500, a profile extrusion process rather than a luminal extrusion process may be employed to provide the desired core structure profile as will be described below.

The illustrated core structure 500 has a number of advantageous features. First, the core structure 500 has a number of receptacles 506 for retaining and separating the wire assemblies 501a,b and 502a,b. In the illustrated embodiment, four receptacles 506 are shown but it will be appreciated that a greater or lesser number of receptacles may be provided depending, for example, on the type of catheter at issue. The illustrated receptacles are formed as longitudinal channels on the external surface of the core structure 500 and are substantially evenly spaced about the periphery of the core structure 500.

The receptacles are dimensioned to receive the wire assemblies 501a,b and 502a,b so that the wires 501a,b and 502a,b are captured between the core structure 500 and the shaft 504 once the core structure 500 and shaft 504 are assembled. In this regard, the various receptacles may be different sizes, e.g., to accommodate different wire sizes and cross-sectional shapes. The core structure 500 also includes a central lumen 508. This lumen 508 accommodates irrigation fluid passageways and/or other structure (e.g., additional wiring) depending on the specific catheter application.

As noted above, it is desired that the catheter shaft have certain mechanical properties, for example, related to incompressibility, torsional rigidity, and flexibility. These properties may vary depending on the particular application. In the illustrated embodiment, the core structure 500 as well as the catheter shaft 504 contributes to defining the properties of the completed catheter assembly.

Thus, in addition to various factors relative to the catheter shaft 504 that affect these mechanical properties, there are a number of relevant factors related to the core structure 500. These include the durometer of the polymer material used to form the core structure 500, the radial thickness of the core structure 500 and the shape of the core structure 500 including the number and size of the receptacles 506 as well as any additional features such as ribs or cut-outs (radially and/or axially extending) that may be provided to alter the mechanical properties or for other purposes.

The illustrated core structure 500 is dimensioned to fit snugly into the lumen of the catheter shaft 504 although the dimensions can vary from application to application as the structure 500 may have, for example, an outside diameter of 0.066 inches and an inside diameter of about 0.042 inches, thus defining a maximum thickness of about 0.012 inches. The illustrated receptacles 506 each have a radial depth of about 0.008 inches (defined relative to a circular reference envelope having the noted outside diameter) and a width of about 0.018 inches. The durometer of the core structure 500 is about 35-72.

Although the core structure can accommodate substantially any number of wires that may be desired by a catheter designer, the illustrated core structure 500 houses four wire assemblies 501*a,b* and 502*a,b*. Specifically, the core structure houses a pair of pull wire assemblies 501*a,b*, and a pair of electrode wire assemblies 502*a,b*. The pull wire assemblies 501*a,b*, which may be of conventional construction generally include a metal wire slidably disposed in a teflon tube. It is noted that the performance of this pull wire is enhanced by maintaining the wires in a fixed, diametrically opposed relative relationship, and the receptacles 506 are highly effective in this regard. The electrode wires assemblies 502*a,b*, which also may be of conventional construction, typically include a conductive wire encased in an insulating coating.

To assemble the catheter, the core structure 500 with the wire assemblies 501*a,b*, and 502*a,b* are inserted into the lumen of the catheter shaft 504. Specifically, the core structure 500 is disposed on a mandrel 510, shown in phantom in FIG. 5. The mandrel 510 may be coated in teflon to facilitate withdrawal of the mandrel 510 after the core structure 500 is fully inserted into the lumen of the catheter shaft 504. The mandrel 510 is then used to advance the core structure 500 and wire assemblies 501*a,b* and 502*a,b* into the catheter shaft 504 as shown in FIG. 6. Thereafter, the mandrel 510 is withdrawn to define lumen 508 of the core structure 500. The pull wire assemblies 501*a,b* and electrode wire assemblies 502*a,b* can then be connected to the electrode tip assembly and the handle set in conventional fashion and additional tip jackets, shrink wrap coatings and the like can be applied as may be desired. The polymer materials may be reflown to secure the shaft/core structure assembly to the electrode tip assembly. It is noted that only reflowing the tip assembly interface is required in this regard, thereby simplifying construction in relation to conventional techniques that typically require reflowing of the full length of the catheter shaft after stringing the wires. Moreover, the construction as described herein results in a sealed electrode that requires little or no trimming.

Figure 7:
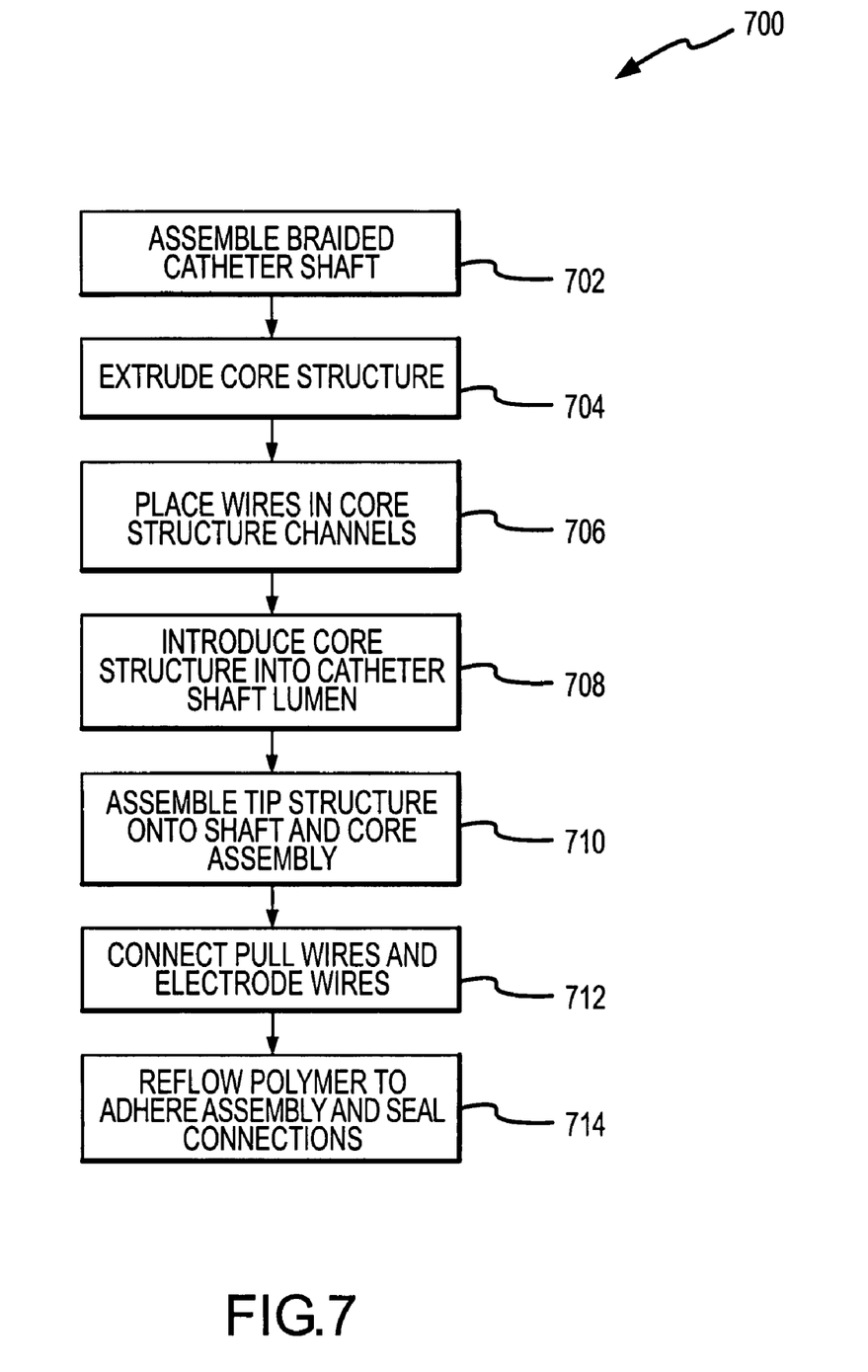
FIG. 7 is a flow chart illustrating a process for constructing a catheter in accordance with the present invention.

This construction process can be summarized by reference to the flow chart of FIG. 7. The process 700 is initiated by assembling (702) the dual braided shaft. As described above, this generally involves a series of extrusion and braiding steps and results in a shaft structure with a central lumen extending therethrough. The core structure is then extruded (704) and the wires are placed (706) into the receptacle channels formed on the external surface of the core structure.

The core structure, which is disposed on a mandrel, together with the wires, are then introduced (708) into the central lumen of the catheter shaft. At this point, an assembled catheter shaft and core assembly is defined. The electrode tip assembly is then assembled (710) onto the shaft/core assembly and the pull wires and electrode wire are connected (712), e.g., mechanically and/or by brazing or welding. The polymer material can then be reflowed (714) at the interface of the shaft/core assembly and the electrode tip assembly to adhere the assemblies and seal the connections.

Although a number of embodiments of this invention have been described above with a certain degree of particularity, those skilled in the art could make numerous alterations to the disclosed embodiments without departing from the spirit or scope of this invention. For example, the invention is not limited to steerable, irrigated ablation catheter applications but is more generally applicable to other catheter types and applications. Moreover, the core structure may be used with other types of catheter shafts and is not limited to dual braided shaft applications. In addition, although a particular core shape and a unitary extruded construction are described above, other core structure shapes, materials and construction may be employed. The discussion above also sets forth a particular construction process involving separate construction sequences for the catheter shaft and core structure followed by assembly of these components, however, it will be appreciated that a single sequence for constructing the overall core structure/catheter shaft assembly may be employed.

All directional references (e.g., upper, lower, upward, downward, outer, inner, axial, radial, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims

What is claimed is:

1. A catheter apparatus comprising:
   a catheter shaft having a first lumen extending therethrough, said first lumen having at least a first inside cross-dimension;
   a first pair of wires and a second pair of wires; and
   a core structure, disposed within said first lumen of said catheter shaft, configured to secure the first pair of wires and the second pair of wires between an inside surface of said catheter shaft and an outside surface of said core structure,
   wherein said core structure includes outside surface portions between locations of the wires having a second cross-dimension that is substantially equal to said first cross dimension of said first lumen for maintaining the core structure in a fixed spatial relationship with respect to the catheter shaft,
   wherein said core structure includes multiple receptacles formed therein for receiving each of said first and second pairs of wires and wherein said multiple receptacles and each of said first and second pairs of wires extend axially through substantially the entirety of the catheter shaft,
   wherein said core structure secures said first and second pairs of wires relative to a section of said catheter shaft substantially free of adhesion between said core structure and said catheter shaft at said section, and
   wherein each wire of said first pair of wires and said second pair of wires are substantially evenly spaced about a periphery of said core structure.

2. The apparatus of claim 1, wherein said core structure is of unitary construction and is formed from a polymer material.

3. The apparatus of claim 1, wherein said core structure has a central lumen formed therein.

4. The apparatus of claim 1, wherein said catheter shaft comprises an inner braid and an outer braid.

5. The apparatus of claim 1, wherein said first pair of wires comprises at least one steering wire configured to steer at least a portion of the catheter apparatus.

6. A catheter apparatus comprising:
   a catheter shaft defining a first lumen;
   a core structure disposed within said catheter shaft; and a first pair of wires and a second pair of wires interposed between an inside surface of said catheter shaft and an outside surface of said core structure, wherein said core structure includes multiple receptacles formed therein for receiving each of said first and second pairs of wires and wherein said multiple receptacles of said core structure and each of said first and second pairs of wires extend axially through substantially the entirety of the catheter shaft, wherein said first and second pair of wires are removably received by said core structure, and wherein each wire of said first pair of wires and said second pair of wires are substantially evenly spaced about a periphery of said core structure.

7. The apparatus of claim 6, wherein said core structure includes outside surface portions having an outside cross-dimension that is substantially equal to an inside cross-dimension of said first lumen for maintaining said core structure in a fixed spatial relationship with respect to said catheter shaft.

8. The apparatus of claim 6, wherein said core structure is of unitary construction and is formed from a polymer material.

9. The apparatus of claim 6, wherein said first pair of wires are operative to move relative to at least one of said catheter shaft and said core structure.

10. The apparatus of claim 6, wherein said core structure has a central lumen formed therein.

11. The apparatus of claim 6, further comprising a catheter tip coupled to said catheter shaft, wherein said first pair of wires comprises at least one steering wire attached to said catheter tip and configured to steer said catheter tip.

12. The apparatus of claim 6, wherein said first pair of wires comprises at least one steering wire configured to steer at least a portion of the catheter.

* * * * *